United States Patent [19]
Takeuchi

[11] Patent Number: 6,095,978
[45] Date of Patent: Aug. 1, 2000

[54] METHOD OF MANUFACTURING AN ULTRASONIC PROBE AND THE ULTRASONIC PROBE AND AN ULTRASONIC IMAGING APPARATUS

[75] Inventor: Yasuhito Takeuchi, Tokyo, Japan

[73] Assignee: GE Yokogawa Medical Systems, Limited, Tokyo, Japan

[21] Appl. No.: 09/169,827

[22] Filed: Oct. 10, 1998

[30] Foreign Application Priority Data

Nov. 11, 1997 [JP] Japan ..................................... 9-308980

[51] Int. Cl.$^7$ ....................................................... A61B 8/00
[52] U.S. Cl. ......................... 600/443; 600/459; 29/25.35
[58] Field of Search .................................. 600/459, 443; 29/25.35; 310/334, 336, 365; 367/140, 155

[56] References Cited

U.S. PATENT DOCUMENTS

| | | | |
|---|---|---|---|
| 5,329,496 | 7/1994 | Smith | 367/140 |
| 5,493,541 | 2/1996 | Snyder | 367/155 |
| 5,553,035 | 9/1996 | Seyed-Bolorforosh et al. | 367/140 |
| 5,704,105 | 1/1998 | Venkataramani et al. | 29/25.35 |

*Primary Examiner*—Francis J. Jaworski
*Attorney, Agent, or Firm*—Moonray Kojima

[57] ABSTRACT

In order to reduce the impedance of an ultrasonic transducer array, an ultrasonic probe is provided in which a plurality of holes 34 are disposed running in the thickness direction of a piezoelectric material plate 32 and electrodes 36 are provided on the internal walls of the holes so as to exploit the ultrasonic vibration of the wall of piezoelectric material between the adjacent holes according to the electromechanical coupling coefficient $k_{31}$. An ultrasonic imaging apparatus employing such an ultrasonic probe is also provided.

8 Claims, 8 Drawing Sheets

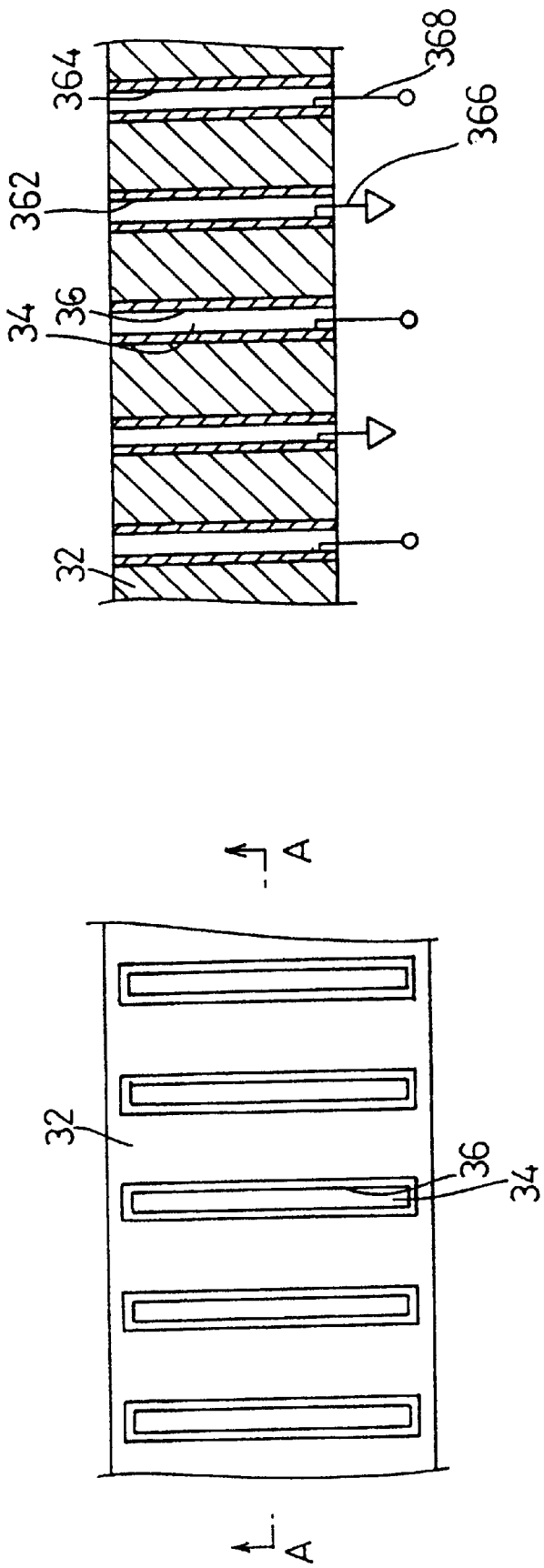

METHOD OF MANUFACTURING AN ULTRASONIC PROBE AND THE ULTRASONIC PROBE AND AN ULTRASONIC IMAGING APPARATUS

BACKGROUND OF THE INVENTION

The present invention relates to a method of manufacturing an ultrasonic probe, the ultrasonic probe and an ultrasonic imaging apparatus. More particularly, the present invention relates to a method of manufacturing an ultrasonic probe exploiting ultrasonic vibration based on the electromechanical coupling coefficient $k_{31}$, the ultrasonic probe and an ultrasonic imaging apparatus using such an ultrasonic probe.

When a subject is scanned by ultrasound and the inside of the subject is imaged based on received echo signals, an ultrasonic probe is used to transmit the ultrasound and receive the echo. The ultrasonic probe has an array of ultrasonic transducers. The ultrasonic transducers are conventionally constructed from piezoelectric ceramic.

The individual ultrasonic transducers are provided with electrodes on the front and rear surfaces of the piezoelectric ceramic, and utilizes ultrasonic vibration in which the direction of the electric signal and the direction of mechanical vibration are the same, i.e., ultrasonic vibration based on the electromechanical coupling coefficient $k_{33}$.

In order to improve the imaging resolution, the piezoelectric ceramic is formed into a microelement. Accordingly, each ultrasound transducer has a long shape whose height is more than 10 times its base side, and has the electrodes on the upper and lower ends of the long shape.

However, the ultrasonic transducer of such structure has high impedance between the electrodes, making it difficult to attain impedance matching of the driving portion and the receiving portion with the cables used to connect these portions.

SUMMARY OF THE INVENTION

It is an object of the present invention to provide a method of manufacturing an ultrasonic probe having small impedance, the ultrasonic probe and an ultrasonic imaging apparatus using such an ultrasonic probe.

In accordance with a first aspect, the present invention provides a method of manufacturing an ultrasonic probe, comprising steps of: disposing a plurality of holes arranged in parallel with each other and running in the thickness direction of a piezoelectric material plate; polarizing the piezoelectric material plate in its thickness direction; and providing electrodes respectively on the internal walls of the plurality of holes in the piezoelectric material plate.

In accordance with a second aspect, the present invention provides an ultrasonic probe comprising: a piezoelectric material plate which is polarized in its thickness direction and in which a plurality of holes are disposed in parallel with each other running in the thickness direction; and electrodes provided respectively on the internal walls of the plurality of holes in the piezoelectric material plate.

In accordance with a third aspect, the present invention provides the ultrasonic probe as described regarding the second aspects, further comprising two kinds of signal leads connected respectively to adjacent ones of the plurality of holes, one of which is a common signal lead.

In accordance with a fourth aspect, the present invention provides an ultrasonic imaging apparatus comprising: an ultrasonic probe for transmitting ultrasound into a subject and receiving its echo; driving means for supplying a drive signal for transmission to the ultrasonic probe; receiving means for receiving a received signal from the ultrasonic probe; and image producing means for producing an image based on the received signal at the receiving means, wherein the ultrasonic probe comprises: a piezoelectric material plate which is polarized in its thickness direction and in which a plurality of holes are disposed in parallel with each other running in the thickness direction; electrodes provided respectively on the internal walls of the plurality of holes in the piezoelectric material plate; and two kinds of signal leads connected respectively to adjacent ones of the plurality of holes, one of which is a common signal lead.

In the inventions as described regarding the second-fourth aspects, it is preferred that the holes are distributed in a two-dimensional manner to construct a two-dimensional array easily.

(Effect)

The present invention exploits ultrasonic vibration based on the electromechanical coupling coefficient $k_{31}$, in which the direction of electric signals corresponds to the thickness direction of the wall between the holes in the piezoelectric material plate, and the direction of mechanical vibration corresponds to the thickness direction of the piezoelectric material plate. Accordingly, the distance between the opposing electrodes is the wall thickness, and therefore the relatively large-area electrodes are opposed at a relatively small distance, resulting in small impedance between the electrodes.

Further objects and advantages of the present invention will be apparent from the following description of the preferred embodiments of the invention as illustrated in the accompanying drawings.

BRIEF DESCRIPTION OF THE DRAWINGS

FIG. 2a and 2b are schematic illustrations of the configuration of an ultrasonic transducer array in accordance with another embodiment of the present invention.

DETAILED DESCRIPTION OF THE INVENTION

Several embodiments of the present invention will now be described in more detail with reference to the accompanying drawings.

Figure 1B:
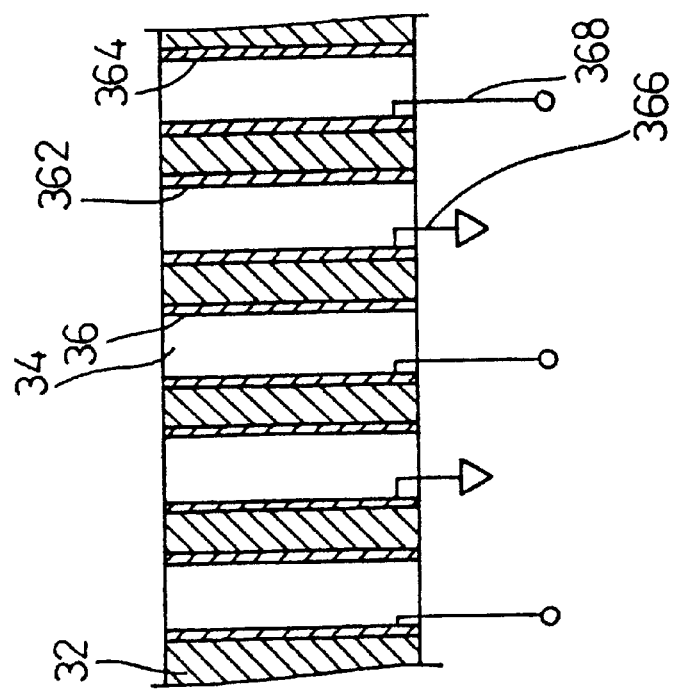
FIG. 1a and 1b are schematic illustrations of the configuration of an ultrasonic transducer array in accordance with one embodiment of the present invention.
Figure 1A:
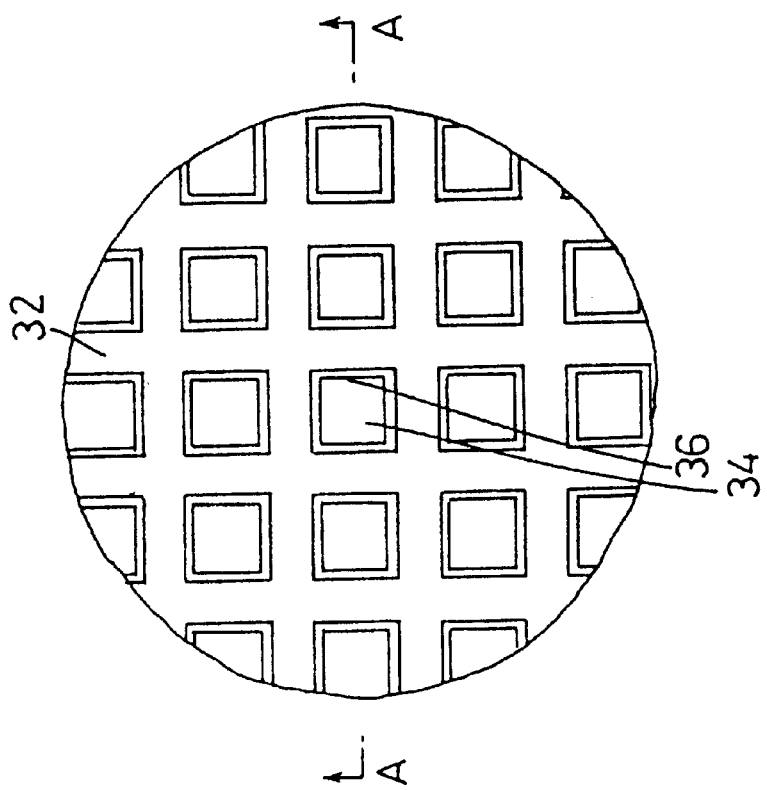

FIG. 1 shows the typical configuration of an ultrasonic transducer array. FIG. 1 (a) is a plan view and (b) is a cross-sectional view taken along line A—A.

As shown, the array is constructed using a piezoelectric material plate 32. The plate 32 is made of, for example, PZT-type piezoelectric ceramic, i.e., lead zirconate titanate (Pb(Zr, Ti)O$_3$), or PT-type piezoelectric ceramic, i.e., lead titanate (PbTiO$_3$). The piezoelectric material plate 32 is polarized in its thickness direction.

The piezoelectric material plate 32 is provided with a plurality of holes 34 running in the thickness direction, arranged in parallel and regularly spaced. The internal wall surface of each of the plurality of holes 34 is clad with an electrode 36. Reference numerals for the hole and the electrode are each shown only at one position for drawing convenience.

In the plurality of holes 34, the electrodes 36 are connected to a common signal lead 366 or an active signal lead 368 so that the electrodes 36 are configured as common electrodes 362 and active electrodes 364 which are arranged alternately both in the vertical direction and in the lateral direction of FIG.1 (a).

Reference numerals for the common electrode, the active electrode and their leads are each shown only at one position for drawing convenience.

Such arrangement of the common electrodes and the active electrodes makes the active electrode 364 and the common electrode 362 opposed to each other between the adjacent holes, separated by the wall of piezoelectric ceramic.

Thus, applying a driving voltage to the active electrode 364 can generate vibration in the thickness direction of the piezoelectric material plate 32 based on the electromechanical coupling coefficient $k_{31}$. Also, external vibration in the thickness direction of the piezoelectric material plate 32 can generate a voltage in the active electrode 364 based on the electromechanical coupling coefficient $k_{31}$. That is, the wall of piezoelectric material between the active electrode 364 and the common electrode 362 acts as an ultrasonic transducer.

By applying a driving voltage to the active electrode 364 at a selected position on the plate surface, the desired ultrasonic transducers within the piezoelectric material plate 32 can be vibrated. Similarly, in response to the external vibration applied to the individual transducers within the piezoelectric material plate 32, a voltage is generated at the corresponding active electrode 364.

Accordingly, the ultrasonic transducer array shown in FIG. 1 can be regarded as a two-dimensional ultrasound transducer array. Such two-dimensional ultrasound transducer array can readily be obtained by perforating the plurality of holes 34 through the piezoelectric material plate 32 and cladding the electrodes 36 on the internal wall of the holes. This technique is significantly convenient.

In such an ultrasonic transducer array, the active electrode 364 and the common electrode 362 are opposed to each other separated by the thickness of the wall between the adjacent holes. The size of the electrodes is relatively large compared to the wall thickness. In other words, the relatively large-area electrodes are opposed at a relatively small distance.

Accordingly, the electrostatic capacity between the electrodes is large and the impedance small. This facilitates impedance matching of the driving and receive portions connected between the active electrode 364 and the common electrode 362, with the cables connecting these.

Although the hole 34 is shown as a tetragonal shape in FIG. 1, the shape of the hole 34 is not limited to a tetragon, and it may be any appropriate shape such as a triangular, hexagonal, circular or any arbitrary shape. Moreover, the hole 34 is not limited to a through-hole as shown, and it may be a closed-ended hole. In addition, the hole 34 may be filled with a conductive material, which is preferable because the signal leads for the active electrodes and common electrodes can be led out more easily by using the conductive material.

Furthermore, the ultrasonic transducer array is not limited to a two-dimensional array and it may be constructed as a one-dimensional array. As shown in FIG. 2, a long piezoelectric material plate 32 is provided with a plurality of holes 34 which are arranged at regular distances in the lengthwise direction, and electrodes 36 are clad on the internal wall surface of the hole 34. The electrodes 36 are configured as common electrodes 362 and active electrodes 364 arranged alternately. The inside of the hole 34 may be filled with a conductive material.

Figure 3:
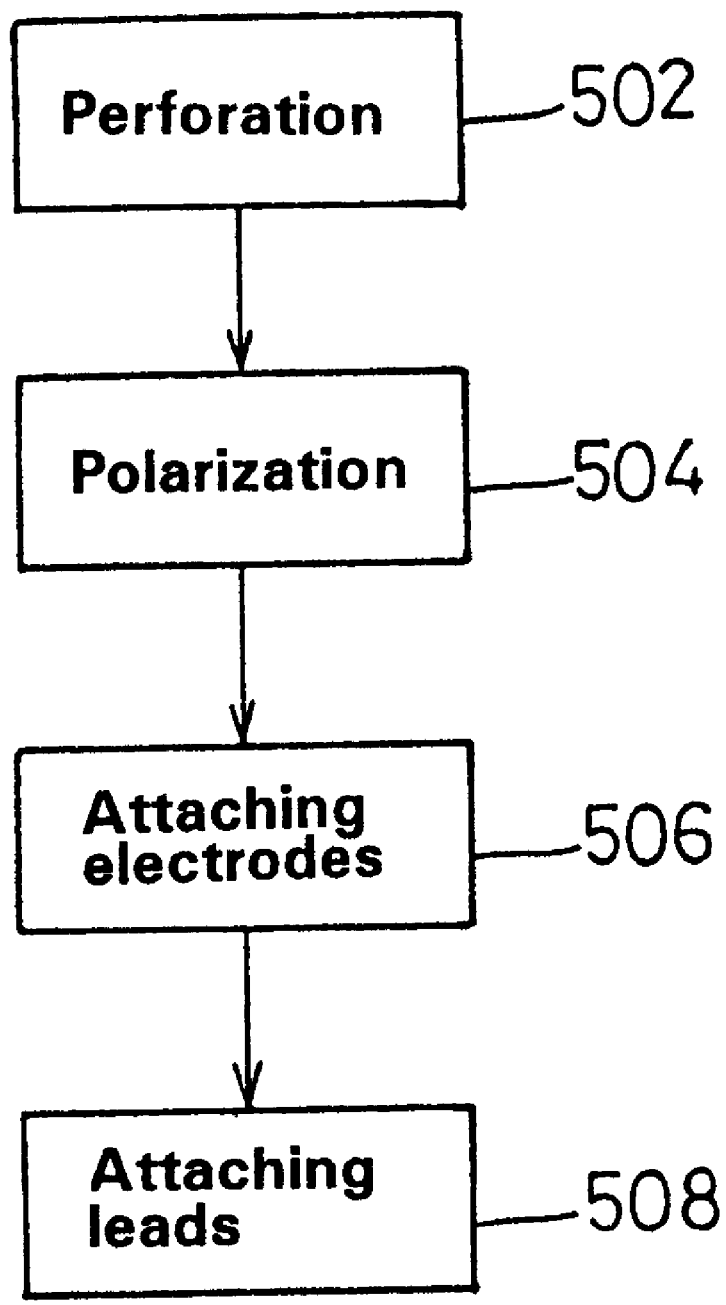
FIG. 3 is a diagram showing a manufacturing process for an ultrasonic transducer array in accordance with one embodiment of the present invention.

Now, description is made on manufacturing such an ultrasonic transducer array. FIG. 3 is an example of a manufacturing process of an ultrasonic transducer array. The process is one embodiment of the present invention.

As shown, perforation through the piezoelectric material plate is first performed in Step 502. The perforation is a process for providing holes 34 through the piezoelectric material plate 32 by an appropriate processing known in the fine processing art, such as the LIGA (lithographic galvanometer) technique based on X-ray lithography, a die stamp technique using a die, or a mechanical perforating process. When the perforation is performed on pre-sintered piezoelectric material, for example, as in the die stamp technique, sintering is performed after the perforation.

Next, the piezoelectric material plate is polarized in Step 504. The polarization is performed by using a polarizing apparatus known in the piezoelectric material art and applying a voltage in the thickness direction of the piezoelectric material plate 32 to polarize the plate 32 in its thickness direction.

In Step 506, the electrodes are clad on the holes. The cladding is a step for cladding a layer of conductive material such as copper or aluminum on the internal surface of the hole 34 by a known technique such as vapor deposition, sputtering or plating.

In Step 508, the leads are attached to the electrodes. This is a step for attaching common signal leads 366 and active signal leads 368 respectively to common electrodes 362 and active electrodes 364 by using a known apparatus such as a wire bonding apparatus.

Figure 4:
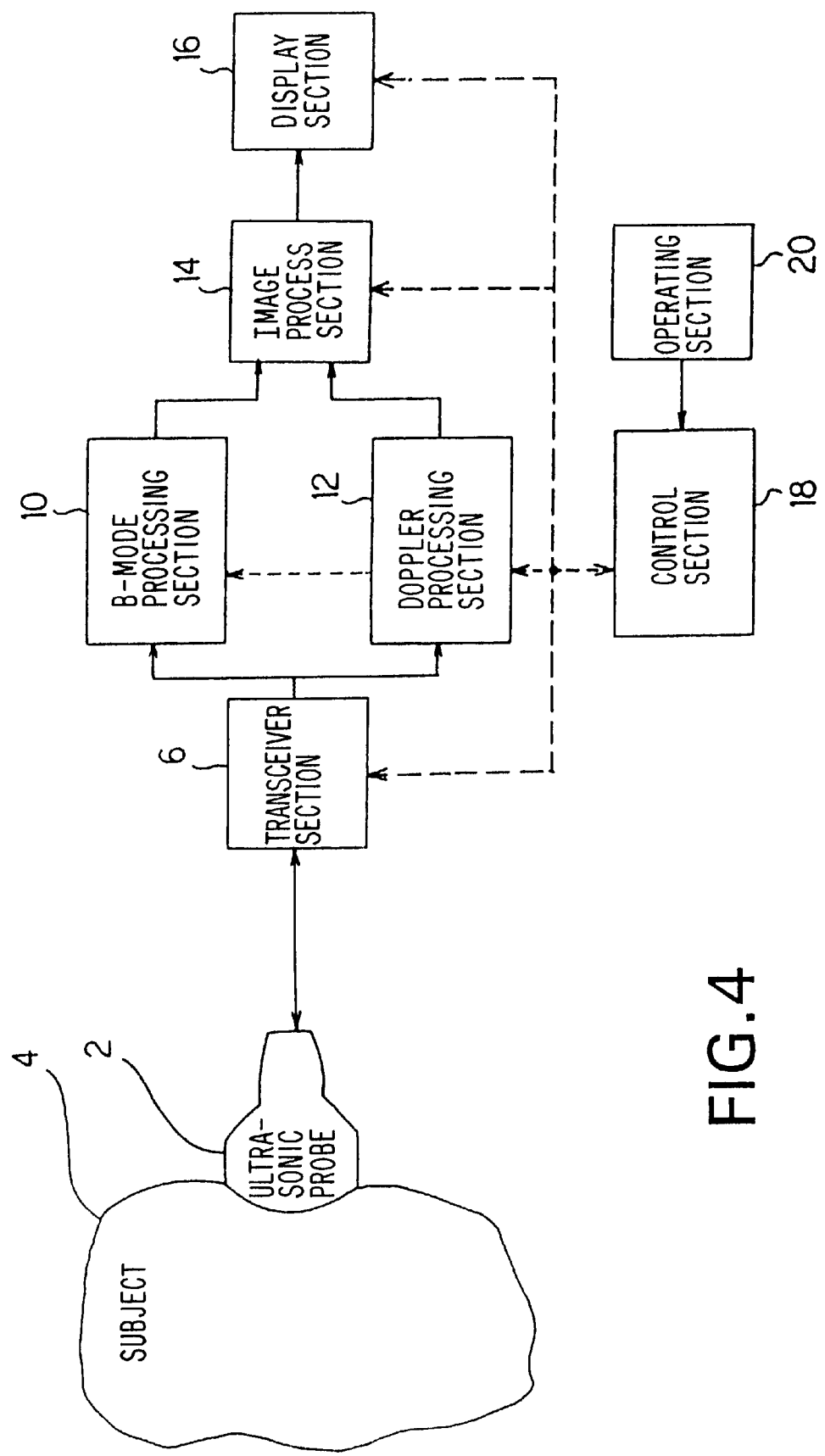
FIG. 4 is a block diagram of an apparatus in accordance with one embodiment of the present invention.

FIG. 4 shows a block diagram of an ultrasonic imaging apparatus. The apparatus is one embodiment of the present invention.

The configuration of the apparatus will now be described. As shown in FIG. 4, the apparatus has an ultrasonic probe 2. The ultrasonic probe 2 has an ultrasonic transducer array configured as shown in FIG. 1 or 2. The ultrasonic transducer array is formed, for example, along an arc bowing frontward. That is, the ultrasonic probe 2 is a convex probe. The ultrasonic probe 2 is used abutted on a subject 4 by an operator.

The ultrasonic probe 2 is connected to a transceiver section 6.

The transceiver section 6 supplies a drive signal to the ultrasonic probe 2 to transmit ultrasound into the subject 4. The transceiver section 6 also receives echo signals impinging upon the ultrasonic probe 2 from the subject 4. Since the impedance of the ultrasonic transducers in the ultrasonic transducer array is low, impedance matching with the transceiver section 6 is easy.

Figure 5:
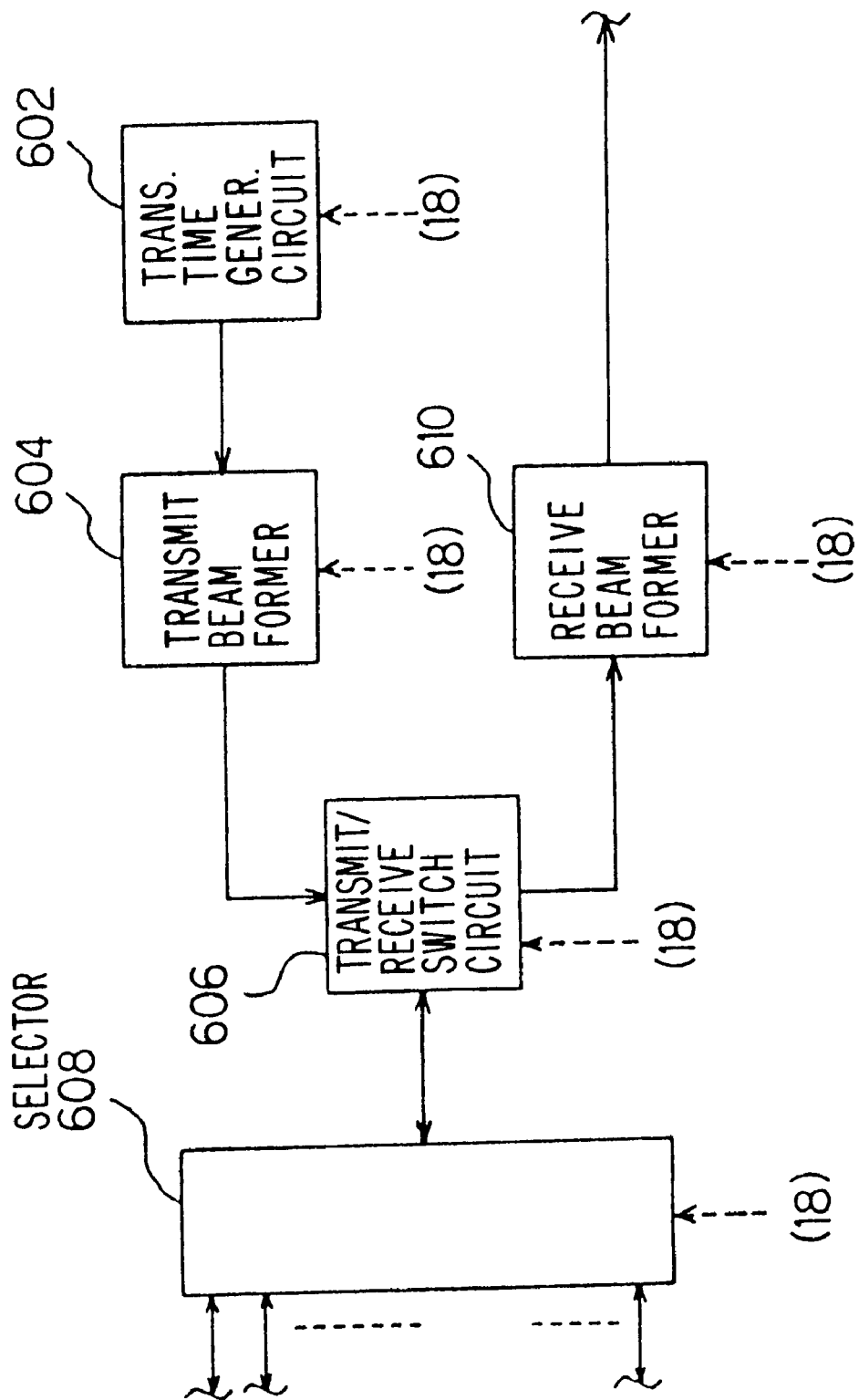
FIG. 5 is a block diagram of a transceiver section in the apparatus in accordance with one embodiment of the present invention.

FIG. 5 shows a block diagram of the transceiver section 6. In the drawing, a transmit timing generation circuit 602 periodically generates transmit timing signals and supplies the signals to a transmit beamformer 604.

The transmit beamformer 604 generates a transmit beam forming signal which is comprised of a plurality of driving signals for driving a plurality of ultrasound transducers in the ultrasound transducer array with specific time lags based on the transmit timing signals, and supplies the signals to a transmit/receive switch circuit 606.

The transmit/receive switch circuit 606 supplies the plurality of drive signals to a selector 608. The selector 608 selects a plurality of ultrasonic transducers from the ultrasonic transducer array which constitute a transmit aperture, and supplies the driving signals respectively to the selected transducers.

The plurality of ultrasonic transducers generates a plurality of ultrasounds which differ in phase corresponding to the respective time lags of the plurality of drive signals. By the wavefront synthesis of the ultrasounds, an ultrasonic beam is formed. The transmit direction of the ultrasonic beam is determined by the transmit aperture selected by the selector 608.

The transmission of the ultrasonic beam is repeatedly performed at constant time intervals determined by the transmit timing signals generated by the transmit timing generation circuit 602. The transmit direction of the ultrasonic beam is sequentially changed by switching the transmit aperture by the selector 608. The inside of the subject 4 is thus scanned by a sound ray formed by the ultrasonic beam. That is, the inside of the subject 4 is scanned in a sound ray-sequential manner.

The selector 608 also selects a plurality of ultrasonic transducers from the ultrasonic transducer array which constitute a receive aperture, and supplies a plurality of echo signals received by the selected ultrasonic transducers to the transmit/receive switch circuit 606.

The transmit/receive switch circuit 606 supplies the plurality of echo signals to a receive beamformer 610. The receive beamformer 610 imparts the time lags to the plurality of echo signals to regulate their phases, and then sums the signals to perform receive beamforming, i.e., to form a received echo signal on a receive sound ray. The receive sound rays are scanned similarly as in the transmission by the selector 608.

Figure 6:
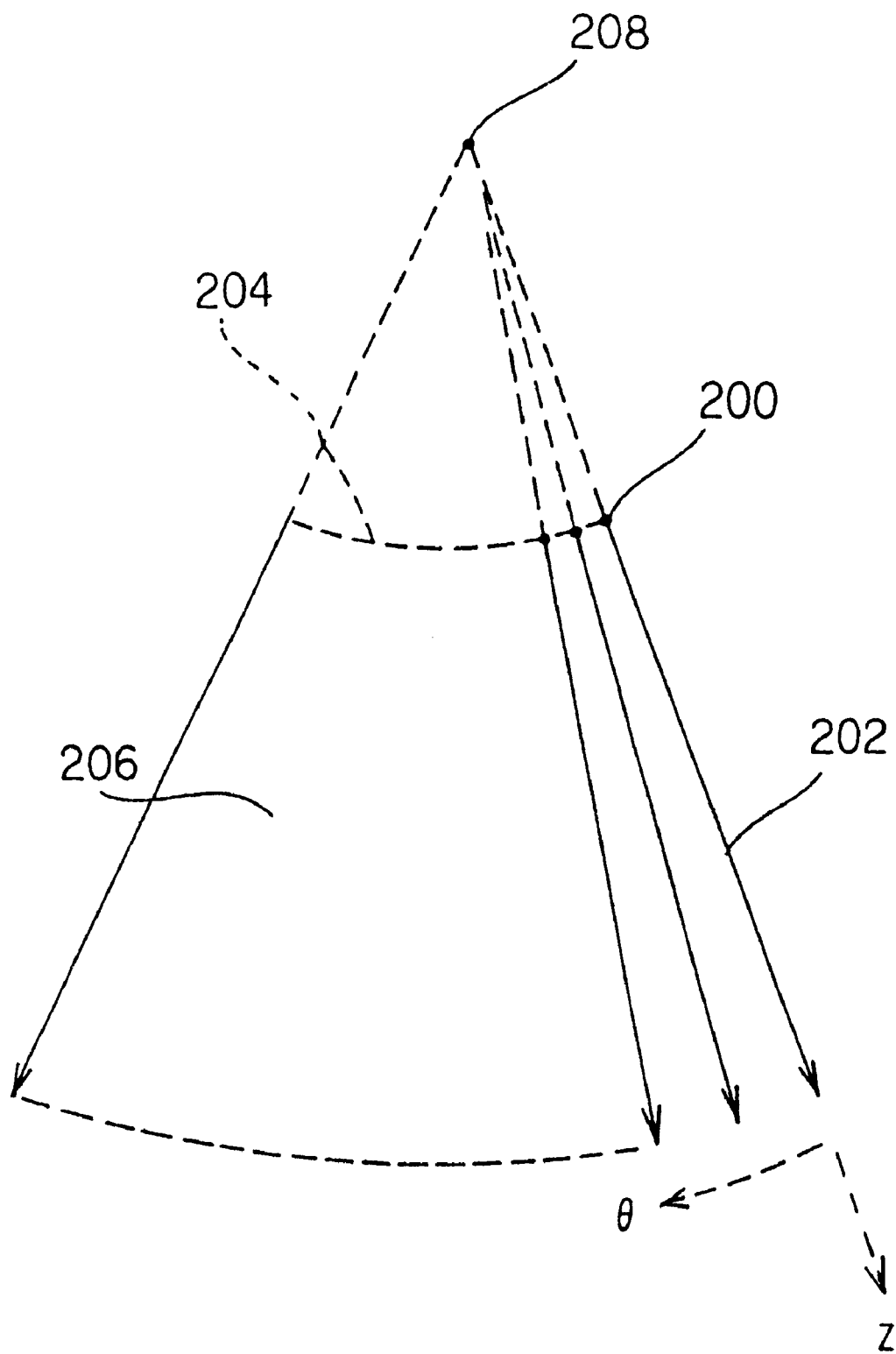
FIG. 6 is a conceptional illustration of sound-ray scanning by the apparatus in accordance with one embodiment of the present invention.

The ultrasonic probe 2 and the transceiver section 6 perform scanning in a manner such as shown in FIG. 6. As a sound ray 202 emanating from an emanation point 200 moves along an arc 204, a fan-shaped two-dimensional region 206 is scanned in the θ direction to perform so-called convex scanning. All the sound rays intersect at one point 208 when the sound rays 202 are extended in the direction opposite to the ultrasound transmit direction (z direction). The point 208 is a divergent point for all of the sound rays.

If the ultrasonic transducer array is a two-dimensional array as shown in FIG. 1, a three-dimensional region can be scanned by sequentially switching the position of the two-dimensional region 206 in the direction perpendicular to the region 206. For the one-dimensional array as shown in FIG. 2, three-dimensional scanning is performed by gradually moving the ultrasonic probe 2 in the direction perpendicular to the two-dimensional region 206.

The transceiver section 6 is connected to a B-mode processing section 10 and a Doppler processing section 12. The received echo signal for each sound ray output from the transceiver section 6 is supplied to the B-mode processing section 10 and the Doppler processing section 12.

Figure 7:
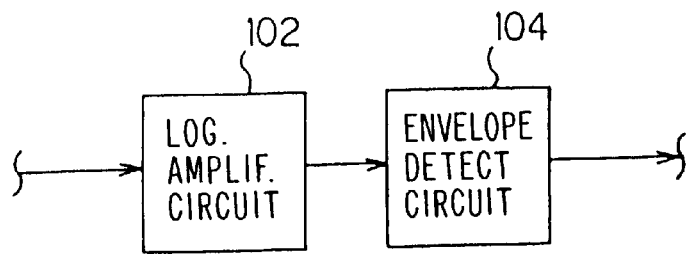
FIG. 7 is a block diagram of a B-mode processing section in the apparatus in accordance with one embodiment of the present invention.

The B-mode processing section 10 produces B-mode image data. As shown in FIG. 7, the B-mode processing section 10 comprises a logarithmic amplification circuit 102 and an envelope detection circuit 104. The section 10 logarithmically amplifies the received echo signal at the logarithmic amplification circuit 102 and detects the envelope of the signal at the envelope detection circuit 104 to obtain a signal representative of the intensity of the echo at each reflective point on the sound ray, i.e., an A-scope signal, whose amplitude at each instant is used as a brightness value to produce the B-mode image data.

Figure 8:
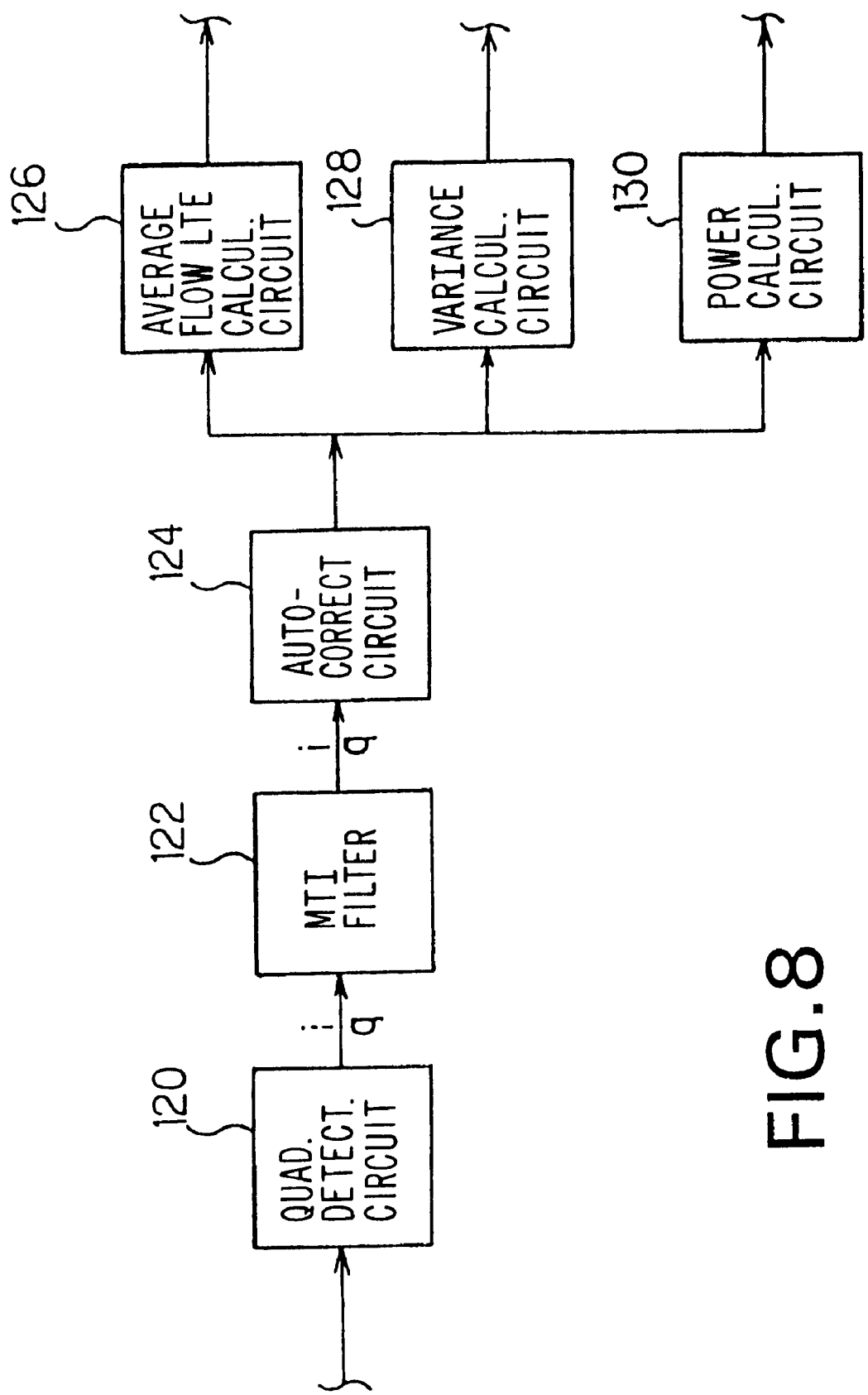
FIG. 8 is a block diagram of a Doppler processing section in the apparatus in accordance with one embodiment of the present invention.

The Doppler processing section 12 produces Doppler image data. As shown in FIG. 8, the Doppler processing section 12 comprises a quadrature detection circuit 120, an MTI (moving target indication) filter 122, an autocorrelation circuit 124, an average flow rate calculation circuit 126, a variance calculation circuit 128 and a power calculation circuit 130.

The Doppler processing section 12 quadrature-detects the received echo signal at the quadrature detection circuit 120, MTI-processes the signal at the MTI filter 122, performs an autocorrelation calculation at the autocorrelation circuit 124, calculates an average flow rate at the average flow rate calculation circuit 126 from the result of the autocorrelation calculation, calculates the variance of the flow rate calculation at the variance calculation circuit 128 from the result of the autocorrelation and calculates the power of the Doppler signal at the power calculation circuit 130 from the result of the autocorrelation calculation.

Thus, the data respectively representing the average flow rate, its variance and the power of Doppler signal for the blood flow inside the subject 4 or the other Doppler signal sources (referred to as "blood flow etc." hereinafter), i.e., the Doppler image data, can be acquired for each sound ray. The flow rate is obtained as a component in the sound ray direction. The flow direction can be distinguished between the approaching direction and the leaving direction.

The B-mode processing section 10 and the Doppler processing section 12 are connected to an image processing section 14. The B-mode processing section 10, the Doppler processing section 12 and the image processing section 14 are one embodiment of the present invention. The image processing section 14 constructs a B-mode image and a Doppler image based on the data respectively supplied from the B-mode processing section 10 and the Doppler processing section 12.

Figure 9:
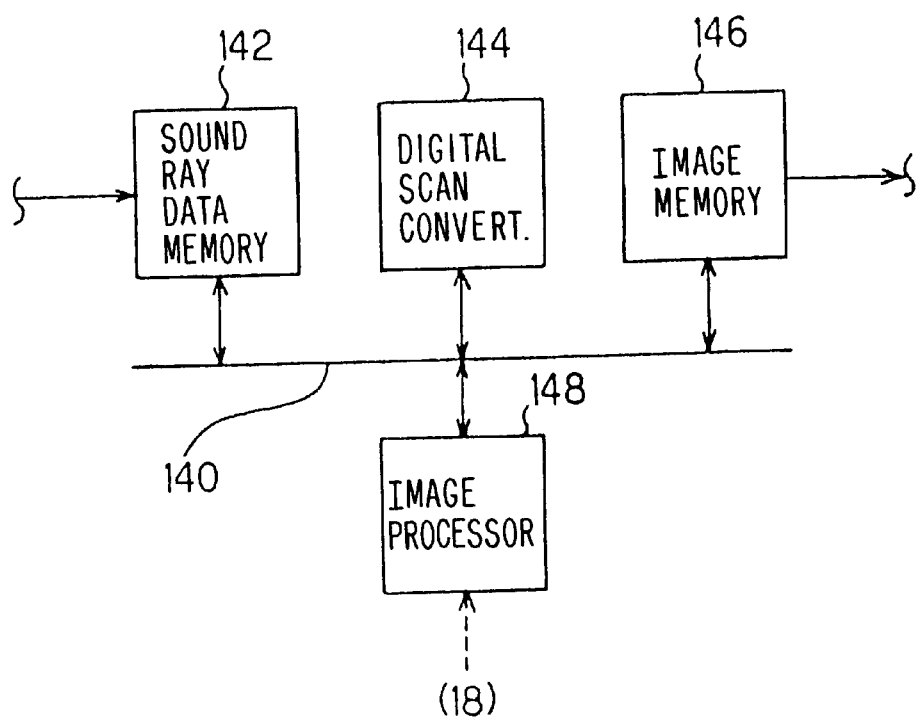
FIG. 9 is a block diagram of an image processing section in the apparatus in accordance with one embodiment of the present invention.

As shown in FIG. 9, the image processing section 14 comprises a sound ray data memory 142, a digital scan converter 144, an image memory 146 and an image processor 148, all of which are connected by a bus 140.

The B-mode image data and the Doppler image data for each sound ray supplied from the B-mode processing section 10 and the Doppler processing section 12 are respectively stored in the sound ray data memory 142.

The digital scan converter 144 converts the data in the sound ray data space into the data in the physical space by the scan conversion. The image data converted by the digital scan converter 144 is stored in the image memory 146. That is, the image memory 146 stores the image data in the physical space. The image processor 148 performs the respective prescribed data processings on the data stored in the sound ray data memory 142 and the image memory 146.

A display section 16 is connected to the image processing section 14. The display section 16 is supplied with an image signal from the image processing section 14, and displays the image based on the image signal. The display section 16 is capable of color display.

The above-described transceiver section 6, B-mode processing section 10, Doppler processing section 12, image processing section 14 and display section 16 are connected to a control section 18. The control section 18 supplies control signals to these sections to control their operation. The control section 18 is also supplied with several information signals from the controlled sections. The B-mode operation and the Doppler mode operation are performed under the control of the control section 18.

An operating section 20 is connected to the control section 18. The operating section 20 is operated by an operator to supply desired commands and information to the control section 18. The operating section 20 includes an operating panel comprising, for example, a keyboard and other operating devices.

The operation of the present apparatus will now be described. The operator puts the ultrasonic probe 2 against the desired part on the subject 4 and operates the operating section 20 to perform imaging in, for example, the combined B-mode and Doppler mode.

The imaging is performed under the control of the control section 18 by time-shared operation in the B-mode and the Doppler mode. For example, the combined scanning is performed by executing the Doppler mode scan several times per B-mode scan.

In the B-mode, the transceiver section 6 scans the inside of the subject 4 in a sound ray-sequential manner via the ultrasonic probe 2 and receives each echo. The B-mode processing section 10 logarithmically amplifies the received echo signal supplied from the transceiver section 6 at the logarithmic amplification circuit 102 and detects its envelope at the envelope detection circuit 104 to obtain an A-scope signal and produce the B-mode image data for each sound ray based on the A-scope signal.

The image processing section 14 stores the B-mode image data for each sound ray supplied from the B-mode processing section 10 into the sound ray data memory 142. Thus, the sound ray data space for the B-mode image data is formed in the sound ray data memory 142.

In the Doppler mode, the transceiver section 6 scans the inside of the subject 4 in a sound ray-sequential manner via the ultrasonic probe 2 and receives each echo. During this operation, the ultrasound transmission and the echo reception are performed a plurality of times per sound ray.

The Doppler processing section 12 quadrature-detects the received echo signal at the quadrature detection circuit 120, MTI-processes the signal at the MTI filter 122, calculates the autocorrelation at the autocorrelation circuit 124, and calculates an average flow rate at the flow rate calculation circuit 126, the variance at the variance calculation circuit 128 and the power at the power calculation circuit 130 from the result of the autocorrelation.

The calculated values form the Doppler image data respectively representing, for example, the average flow rate of the blood flow etc., its variance and the power of the Doppler signal for each sound ray. The MTI processing at the MTI filter 122 is performed using the received echo signals acquired by receiving the echo a plurality of times per sound ray.

The image processing section 14 stores the Doppler image data for each sound ray supplied from the Doppler processing section 12 in the sound ray data memory 142. Thus, the sound ray data space for the Doppler mode image data is formed in the sound ray data memory 142.

The image processor 148 scan-converts respectively the B-mode image data and the Doppler image data in the sound ray data memory 142 at the digital scan converter 144 and writes the converted data to the image memory 146. At that time, the Doppler image data is written as the image data for a CFM (color flow mapping) image in which the variance is combined with the flow rate, and the image data for a power Doppler image.

The image processor 148 writes the B-mode image, the CFM image and the power Doppler image in the separate regions in the image memory 146. The B-mode image shows a tomographic image of the internal tissue in the scanning plane. The CFM image shows the two-dimensional distribution of the rate of the blood flow etc. in the scanning plane. The power Doppler image shows the location of the blood flow etc. in the scanning plane.

The operator operates the operating section 20 to display, for example, a superimposed image of the B-mode image and the CFM image on the display section 16. Accordingly, the CFM image of the blood flow etc. is displayed in color against the background of the tomographic image of the internal tissue represented by the B-mode image.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic probe comprising:

a piezoelectric material plate having oppositely defined planar surfaces and a plurality of rectangular cylindrical through holes defined therein with axes of said cylindrical holes being disposed parallel to each other in a thickness direction perpendicular to said parallel surfaces, said plurality of cylindrical holes being disposed in a regular pattern of parallel columns and rows, as viewed from a surface of said plate, and extending between said oppositely defined planar surfaces;

said plate being polarized in said thickness direction;

a layer of conductive electrode disposed separately on the walls only of each of said cylindrical holes and between said planar surfaces of said plate;

first means for connecting a lead to a first particular conductive electrode disposed on the wall of at least one cylindrical hole; and second means for connecting a lead to a second particular conductive electrode disposed on the wall of at least one other cylindrical hole next adjacent to said at least one cylindrical hole;

whereby a transducer is formed by said first and second particular conductive electrodes and the piezoelectric material disposed therebetween, said first and second particular conductive electrodes being of relatively large dimensions as compared to a small distance therebetween of said piezoelectric material, so that electrostatic capacity between said first and second particular conductive electrodes is large and impedance is small, thereby facilitating impedance matching between the first and second particular conductive electrodes.

2. The probe of claim 1, wherein means are provided for accessing a plurality of first means and second means so as to form a two dimensional transducer array.

3. The probe of claim 1, wherein said cylindrical holes are filled with conductive material in contact with said conductive electrodes on the walls of said cylindrical holes.

4. The probe of claim 1, wherein said piezoelectric material has an electromechanical coupling coefficient $k_{31}$.

5. Method of manufacturing an ultrasonic probe comprising the steps of:

providing a flat piezoelectric material plate having oppositely disposed planar surfaces;

perforating said plate to provide a plurality of holes therein, said plurality of holes being rectangular in shape and extending from one surface to the other surface of said plate, and being disposed in a regular pattern of parallel columns and rows, as viewed from a surface of said plate, wherein the distance between adjacent holes is small and the area of the adjacent walls of adjacent holes is large, said perforating being performed by a method selected from the group consisting of X-ray lithography, die stamping, and mechanical perforating;

applying a voltage in a thickness direction of said plate to polarize said plate in said thickness direction;

providing a separate layer of conductive material on the walls only of each of said plurality of cylindrical holes, utilizing a method selected from the group consisting of vapor deposition, sputtering, and plating; and attaching a separate lead to each of said conductive layers of each hole.

6. The method of claim 5, wherein said piezoelectric material has an electromechanical coupling coefficient $k_{31}$.

7. An ultrasonic imaging apparatus comprising:

an ultrasonic probe for transmitting ultrasound into a subject and for receiving echoes thereof;

driving means for supplying a drive signal for transmission to said ultrasonic probe;

receiving means for receiving a received signal from said ultrasonic probe; and image producing means for producing an image based on said received signal at said receiving means; said ultrasonic probe comprising:

a piezoelectric material plate having oppositely defined planar surfaces and a plurality of rectangular cylindrical through holes defined therein with axes of said cylindrical holes being disposed parallel to each other in a thickness direction perpendicular to said parallel surfaces, said plurality of cylindrical holes being disposed in a regular pattern of parallel columns and rows, as viewed from a surface of said plate, and extending between said oppositely defined planar surfaces;

said plate being polarized in said thickness direction;

a layer of conductive electrode disposed separately on the walls only of each of said cylindrical holes and between said planar surface of said plate;

first means for connecting a lead to a first particular conductive electrode disposed on the wall of at least one cylindrical hole; and second means for connecting a lead to a second particular conductive electrode disposed on the wall of at least one other cylindrical hole next adjacent to said at least one cylindrical hole;

whereby a transducer is formed by said first and second particular conductive electrode and the piezoelectric material disposed therebetween, said first and second particular conductive electrodes being of relatively large dimensions as compared to a small distance therebetween of said piezoelectric material, so that electrostatic capacity between said first and second particular conductive electrodes is large and impedance is small, thereby facilitating impedance matching between the first and second particular conductive electrodes.

8. The apparatus of claim 7, wherein said piezoelectric material has an electromechanical coupling coefficient $k_{31}$.

* * * * *